United States Patent
Foryciarz et al.

(10) Patent No.: US 12,119,089 B2
(45) Date of Patent: *Oct. 15, 2024

(54) GENERATION AND USE OF SIMULATED GENOMIC DATA

(71) Applicants: Agata Foryciarz, Warsaw (PL); Dennis A. Dean, II, Wenham, MA (US)

(72) Inventors: Agata Foryciarz, Warsaw (PL); Dennis A. Dean, II, Wenham, MA (US)

(73) Assignee: SEVEN BRIDGES GENOMICS, INC., Cambridge, MA (US)

( * ) Notice: Subject to any disclaimer, the term of this patent is extended or adjusted under 35 U.S.C. 154(b) by 1138 days.

This patent is subject to a terminal disclaimer.

(21) Appl. No.: 16/841,238

(22) Filed: Apr. 6, 2020

(65) Prior Publication Data

US 2020/0234797 A1    Jul. 23, 2020

Related U.S. Application Data (63) Continuation of application No. 15/383,102, filed on Dec. 19, 2016, now Pat. No. 10,629,292.

(51) Int. Cl.
| | |
|---|---|
| *G01N 33/48* | (2006.01) |
| *G16B 5/00* | (2019.01) |
| *G16B 20/00* | (2019.01) |
| *G16B 20/20* | (2019.01) |
| *G16B 45/00* | (2019.01) |
| *G16B 50/00* | (2019.01) |
| *G16B 50/30* | (2019.01) |

(52) U.S. Cl.
CPC .............. *G16B 45/00* (2019.02); *G16B 5/00* (2019.02); *G16B 20/00* (2019.02); *G16B 20/20* (2019.02); *G16B 50/00* (2019.02); *G16B 50/30* (2019.02)

(58) Field of Classification Search
None
See application file for complete search history.

(56) References Cited

U.S. PATENT DOCUMENTS

| | | | |
|---|---|---|---|
| 5,511,158 | A | 4/1996 | Sims |
| 6,823,299 | B1 | 11/2004 | Contreras et al. |
| 2004/0126840 | A1 | 7/2004 | Cheng et al. |
| 2015/0112658 | A1* | 4/2015 | Kural .................. G16B 30/00 703/11 |
| 2015/0142465 | A1 | 5/2015 | Vaske et al. |
| 2015/0227685 | A1* | 8/2015 | Kural .................. C12Q 1/6869 702/19 |

OTHER PUBLICATIONS

1000 Genomes Project Consortium, A global reference for human genetic variation, vol. 526, Nature.

Baker et al, SiLiCO: A Simulator of Long Read Sequencing in PacBio and Oxford Nanopore, 2016, bioRxiv.
Bartenhagen et al, RSVSim: an R/Bioconductor package for the simulation of structural variations, 2013, pp. 1679-1681, vol. 29, Oxford University Press.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Escalona et al, A comparison of tools for the simulation of genomic nextgeneration sequencing data, 2016, vol. 17, Nature Reviews Genetics.
Gaziano et al, Million Veteran Program: A mega-biobank to study genetic influences on health and disease, 2016, vol. 70, Journal of Clinical Epidemiology.
Hendricks et al., A comparison of Gene Region Simulation Methods, 2012, vol. 7, PLoS ONE.
Hu et al, pIRS: Profile-based Illumina pair-end reads simulator, 2012, vol. 28, Oxford University press.
Huang et al, ART: a next generation sequencing read simulator, 2012, vol. 28, Oxford University Press.
Ivakhno et al, tHapMix: simulating tumour samples through haplotype mixtures, 2016, vol. 33, Oxford University Press.
Koller et al, Probabilistic Graphical Models (Chapter 2), 2009, MIT Press.
Li et al, GWAsimulator: a rapid whole-genome simulation program, 2007, vol. 24, Oxford University Press.
Montana, HapSim: a simulation tool for generating haplotype data with pre-specified allele frequencies and LD coefficients, 2005, pp. 4309-4311, vol. 21, Oxford University Press.
Pattnaik et al, SInC: an accurate and fast error-model based simulator for SNPs, Indels, and CNVs couples with a read generator for short-read sequence data, 2014, vol. 15, BMC Bioinformatics.
Purcell et al, Plink: A Tool Set for Whole-Genome Association and Population-Based Linkage Analyses, 2007, vol. 81, The American Journal of Human Genetics.
Richter et al, MetaSim—A Sequencing Simulator for Genomics and Metagenomics, 2008, vol. 3, PLoS ONE.

(Continued)

*Primary Examiner* — Anna Skibinsky (74) *Attorney, Agent, or Firm* — Morgan, Lewis & Bockius LLP (57) ABSTRACT

Embodiments of the invention utilize a graph-based approach for simulating genomic datasets from large scale populations. Genomic data may be represented as a directed acyclic graph (DAG) that incorporates individual sample data including variant type, position, and zygosity. A simulator may operate on the DAG to generate variant datasets based on probabilistic traversal of the DAG. This probabilistic traversal reflects genomic variant types associated with the subpopulation used to build the DAG, and as a result, the generated variant datasets maintain statistical fidelity to the original sample data.

21 Claims, 3 Drawing Sheets

(56) References Cited

OTHER PUBLICATIONS

Rosenberg, MySSP: Non-stationary evolutionary sequence simulation, including indels, 2005, vol. 1, Evolutionary Bioinformatics Online.

* cited by examiner

GENERATION AND USE OF SIMULATED
GENOMIC DATA

RELATED APPLICATION

This application is a continuation of U.S. patent application Ser. No. 15/383,102, filed Dec. 19, 2016.

TECHNICAL FIELD

Embodiments of the present invention relate generally to the analysis and use of bioinformatic data, e.g., data obtained by sequencing a nucleic acid.

BACKGROUND

The science of bioinformatics applies sophisticated analytic techniques to biological data, such as genome sequences, to better understand the underlying biology. In order to benchmark and refine bioinformatic techniques, they are applied to known "reference" sequences—e.g., a particular genomic region or even a complete genome. These sequences may be completely empirical, i.e., obtained by biochemically sequencing actual genomes from a population of organisms. Although validation of a bioinformatic technique with empirical data is ultimately essential, as it represents real organisms, there may simply not be enough of it. For example, sequence data for particular genomic regions in a specific subpopulation of interest (e.g., African American veterans with a history of heart disease) may not be widely available, at least not from many individuals, due both to resource limitations and patient-privacy concerns.

If some true sequences are known along with the statistical principles underlying intrasequence variation among individuals within a group, it is possible to generate simulated data for benchmarking and analysis purposes. A small amount of real data, in other words, can be used to generate a large amount of simulated data with reasonable fidelity to the biology of the subpopulation. Therefore, computer simulation of genetic and genomic data has become increasingly popular for assessing and validating biological models or for gaining an understanding of specific data sets.

Human genomic variants are nucleotide sequences that differ from the human genome reference, a sequence of over 3 billion nucleotides represented by the letters A, T, C, and G. Genomic variant types include single-nucleotide polymorphisms, structural variants, insertions and deletions (see definitions below). The variants of a subpopulation define its particular genomic characteristics, and the objective of a simulation is to preserve the frequency of these variants in the simulated data. Current simulation frameworks are limited by the types of variants they incorporate, their scalability, accuracy, speed, and/or their support for relatively small subpopulations within a larger group. Accordingly, there is a need for techniques and systems for generating statistically valid simulated genomic data that respects variant patterns within a subpopulation and which overcome or mitigate these limitations.

TERMINOLOGY

The sequences of primary concern herein involve nucleic acids, i.e., deoxyribonucleic acid (DNA) and ribonucleic acid (RNA). The following explanations are provided for ease of understanding, but it should be understood that there is no intention to alter existing art-recognized definitions.

An "allele" refers to one of two or more alternative forms of a gene that arise by mutation and are found at the same place on a chromosome. "Diploid" organisms, such as humans, have two complete sets of chromosomes, and an individual is "homozygous" for a particular gene if identical alleles of the gene are present on both copies of the relevant chromosome. An individual is "heterozygous" for the gene if these chromosomes contain different alleles. "Zygosity" refers to whether an individual is homozygous or heterozygous for a gene. Matched chromosomes or portions thereof are often referred to as "strands," which are not to be confused with the complementary strands of a single length of DNA.

Variations between genes may be studied at the nucleotide level. A single-nucleotide polymorphism ("SNP") is a variation in a single nucleotide that occurs at a specific position in the genome, where each variation is present to some appreciable degree within a population. An SNP may involve an insertion or deletion of a nucleotide relative to the reference sequence. SNPs, insertions, and deletions collectively represent "genomic variant types." Insertions and deletions are referred to generically as "InDels." A set of variations that often occur together on the same chromosome may be referred to as a "haplotype" sequence, or haplotype. Variant Call Format (VCF) is a tabular format that lists a variant and individual genotypes in each line; see, e.g., https://samtools.github.io/hts-specs/VCFv4.2.pdf.

In graph theory, a "graph" is a representation containing a series of vertices or nodes connected by edges. In a "directed" graph, the edges have a direction associated with them. A "directed acyclic graph" or "DAG" contains no loops (i.e., there is no way to start at any vertex and follow a sequence of directed edges that eventually loops back to the original vertex). DAGs can model many different kinds of information. A spreadsheet can be modeled as a DAG, for example, with a vertex for each cell and an edge whenever the formula in one cell uses the value from another.

SUMMARY

Various embodiments of the invention provide a graph-based approach for simulating genomic datasets from large-scale populations—e.g., populations of thousands, tens of thousands, or even millions of organisms. Genomic data may be represented as a DAG that incorporates individual sample data including variant type, position, and zygosity. A simulator may operate on the DAG to generate variant datasets based on probabilistic traversal of the DAG. This probabilistic traversal reflects genomic variant types associated with the subpopulation used to build the DAG, and as a result, the generated variant datasets maintain statistical fidelity to the original sample data. It should be noted that the "genome simulation" produced by graph traversal in accordance herewith simulates a set of variants for an individual. This can be expanded, if desired, into simulations of actual sequence reads.

Unlike many conventional techniques, the approaches described herein are scalable to large populations. A DAG is an extremely compact and efficient way to store a plurality of genomes. DAGs are also easily updated (e.g., via a hash function as described below) to add new variants or update counts of variants already present, and enable analyses of a sub-population in a way that a large number of individual data sets would not (e.g., by storing several sub-populations separately as separate DAGs, or generating DAGs with mixtures of several sub-populations). Simulated variant datasets may be very close to those from which the DAG is created, maintaining genomic variant data and zygosity; for example, variant frequency may be reproduced within 1% on average. In some embodiments, a hash function may encode genomic position and allele type, which facilitates rapid search and determination whether an allele is present in the graph. Advantages of the invention include flexibility, scalability, accuracy and speed relative to conventional solutions.

Accordingly, in a first aspect, the invention pertains to a method of simulating genomic data using input data representing nucleic-acid sequences obtained by chemical analysis of biological samples obtained from a population of organisms, where the population exhibits a variant frequency. In various embodiments, the method comprises the steps of (a) computationally representing the input data as a DAG comprising a plurality of nodes and edges connecting the nodes, wherein the nodes include an origin node and a terminus node, each node corresponds to a genomic position and a variant, and the edges have weights corresponding to the occurrences of nodes connected by edges in the input data; and (b) repeatedly (i) traversing a sequence of nodes of the DAG starting from the origin node and terminating with the terminus node, the traversal being performed probabilistically in accordance with the edge weights; and (ii) storing, in a database, simulated genomic data corresponding to the traversal and retaining the variant frequency of the population.

In various embodiments, each node further comprises zygosity information. The traversals may be performed using a weighted random function. In some embodiments, wherein the population simulator is configured to repeat (i) and (ii) for a plurality of populations In some embodiments, the method further comprises the step of computationally representing input data from each of the populations as a separate DAG, and step (b) is performed on the separate DAGs to simulate individuals from each population. The method may further include the step of using a hash function to assign a hash value to each of the nodes, where the hash value is based on the genomic position and variant associated with the node.

In various embodiments, the computational representation step comprises initializing the DAG and repeatedly adding entries to the DAG or changing weights associated with existing entries by performing union operations on the DAG and a new entry. Each node may also comprise zygosity information, and entries may be added according to steps comprising reading in a variant pair as a node, assigning a hash value to the node, the hash value being based at least in part on a genomic position and a zygosity of the variant pair associated with the node, and performing a union operation using the node hash value to determine if the variant pair associated with the node is already in the DAG, and if not, increasing a weight of at least one edge of the DAG that connects to the node. The DAG may be created using a set of genotypes for each individual organism in the population.

In various embodiments, the simulated genomic data may be a simulated genome, a simulated genome subset, a simulated chromosome, or a list of simulated genomic variants. The DAG may not include variants that are homozygous for the reference.

In some embodiments, computationally representing the input data as a DAG further comprises calculating haplotypes from the input data, where each haplotype may be computationally represented in the DAG as a node. A haplotype may comprise a set of variants that are statistically correlated with one another.

In another aspect, the invention pertains to a system for simulating genomic data using input data representing nucleic-acid sequences obtained by chemical analysis of biological samples obtained from a population of organisms, where the population exhibits a variant frequency. In various embodiments, the system comprises a computer memory; a graph generator for computationally representing the input data as a data structure encoding a DAG comprising a plurality of nodes and edges connecting the nodes, wherein the nodes include an origin node and a terminus node, each node specifies a genomic position and a variant type, and the edges have associated weights corresponding to the occurrences of nodes connected by edges in the input data; and a population simulator for simulating variant datasets by repeatedly (i) traversing a sequence of nodes of the DAG starting from the origin node and terminating with the terminus node, the traversal being performed probabilistically in accordance with the edge weights, and (ii) storing, in the computer memory, simulated genomic data corresponding to the traversal and retaining the variant frequency of the population.

In various embodiments, each node further comprises zygosity information. The population simulator may be configured to traverse the sequence of nodes using a weighted random function. In various embodiments, the population simulator is configured to repeat (i) and (ii) for a plurality of populations. The graph generator may be configured to computationally represent input data from each of the populations as a separate DAG, and the population simulator may be configured to simulate individuals from each separate DAG.

In some embodiments, the graph generator is further configured to use a hash function to assign a hash value to each of the nodes in the data structure, where the hash value is based on the genomic position and variant associated with the node. The graph generator may be configured to initialize the DAG and repeatedly add entries thereto or change weights associated in the data structure with existing entries by performing union operations on a the DAG and a new entry.

In various embodiments, each node also comprises zygosity information and the graph generator is configured to add entries by temporarily storing, in the data structure, a variant pair as a node, assigning a hash value to the node, the hash value being based at least in part on a genomic position and a zygosity of the variant pair associated with the node, and performing a union operation using the node hash value to determine if the variant pair associated with the node is already in the DAG, and if not, increasing a weight of at least one edge of the DAG that connects to the node.

The simulated genomic data may be a simulated genome, a simulated genome subset, a simulated chromosome, or a list of simulated genomic variants. The graph generator is further configured to not include homozygous reference variants in the DAG.

The term "substantially" or "approximately" means ±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1:
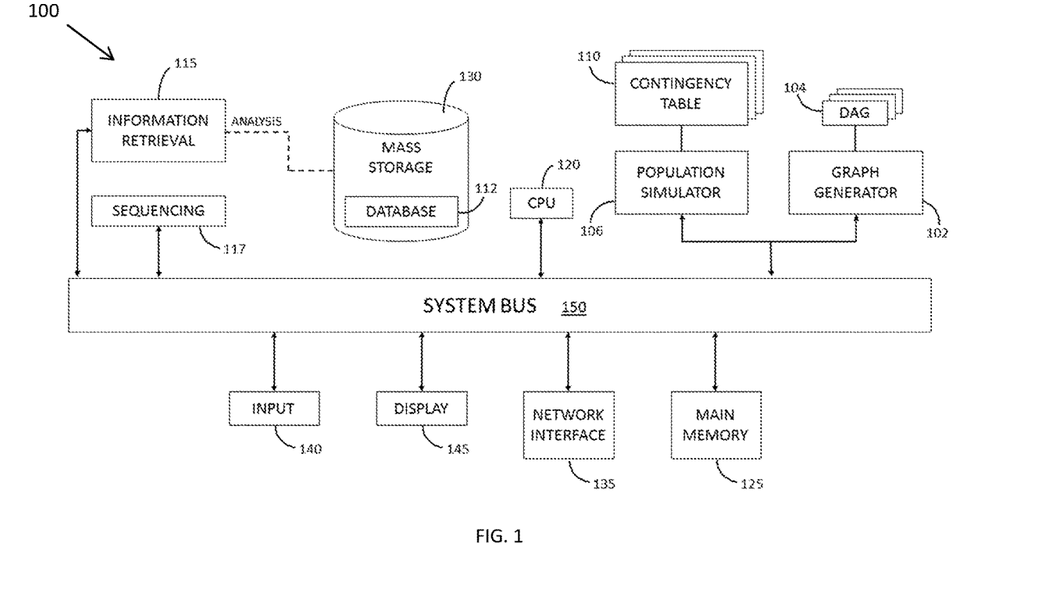
FIG. 1 is a block diagram of a representative computational architecture for implementing embodiments of the present invention.

The general approach taken by embodiments of the present invention is illustrated in FIG. 1, which illustrates, in block-diagram form, an exemplary computer 100 with features enabling it to generate simulated genomic data and also to exploit that data following generation thereof. The computer 100 includes a graph generator 102, which takes variant information (typically in VCF format) and generates a corresponding DAG 104 with relevant variants (as described in greater detail below). A population simulator 106 simulates variant datasets by graph traversal of the previously generated DAG 104. Importantly, the probability of traversing any particular edge of the DAG depends on the frequency with which it was found in the sample data. This information may be represented as a contingency table 110. The simulator 106 may perform sampling from the contingency table, returning a set of traversed nodes for each traversal. These nodes may be stored in a database 112, e.g., following conversion to VCF format. The data may be analyzed by an information retrieval and analysis unit 115, which may be hosted as software within the computer 100 or may be an external component.

In some embodiments, the output data corresponds to simulated whole genomes (e.g., in the form of a list of variants, VCF files, or even simulated sequencing reads for that simulated genome) that facilitate development and evaluation of data-analysis programs, or that can be used for preliminary or offline analyses. Simulating whole genomes is of particular importance given the difficulty of obtaining real data given patient and research subject privacy concerns. Information retrieval and analysis unit 115 can be configured to, for example, test hypotheses offline in order to design a study that will use actual data obtained from specific individuals; determine the number of genomes needed for a particular analysis (i.e., a "power" analysis); and benchmark bioinformatics tools.

In one representative implementation, information retrieval and analysis unit 115 is configured to perform cross validation and sampling approaches for a proposed study. For example, the unit 115 may run a simulation and a corresponding analytical test multiple times and evaluate whether similar results are obtained for each. For example, it is possible to test whether the number of individuals in a population is sufficient to provide meaningful data from an association study trying to correlate observed phenotypes with genotypes. If the simulation is run once and produces a p-value indicating significance (e.g., <0.05), and then is run again and produces a p-value indicating no significance (e.g., >0.05), the study parameters may not be trustworthy; knowing this in advance prevents resources from being wasted on real data once it is available, and provides a much more rigorous test of significance than could be obtained simply by running the analytical test once on the real data.

Typically, the simulated data stored in database 112 is a list of variants for a genome. Numerous available applications operate directly from a list of variants, such as genome-wide association studies. As noted above, using simulated whole genomes (as opposed to downloading and storing publicly available whole genome sequences) provides significant computational efficiency and reliability benefits for testing and benchmarking such applications given the known (indeed, custom-tailored) data characteristics, the limited load on local computational and storage resources (as genomes can be created as needed, on the fly) and the lack of need for security measures (that would be necessary, for example, to protect patient privacy in the case of real data).

The techniques and systems discussed herein can also be used to generate mixed populations of heterogeneous genomes for algorithm testing, or simulated whole genomes for testing or benchmarking a sequence read simulator (e.g., the MITTY bioinformatics testing and benchmarking suite, available at http://latticelabs.githubio/Mitty). In this case, the simulated sequence reads would be for that simulated genome, and could further be used to benchmark both sequencing alignment and variant calling tools. Precision and recall can be readily computed because the data includes the truth set (variants in the simulated genome).

The operation of computer 100 is directed by a central-processing unit ("CPU") 120. A main system memory 125, generally implemented as a bank of random-access memory (RAM), stores the runtime versions of graph generator 102 and population simulator 106. More generally, main memory 125 contains instructions that control the operation of CPU 120 and its interaction with other hardware components. An operating system directs the execution of low-level, basic system functions such as memory allocation, file management and operation of one or more mass storage devices 130, typically one or more nonvolatile disk drives. A mass storage device 130 may host database 112, although it should be understood that the database need not be local. A network interface 135 facilitates interaction with other computers and resources (permitting, for example, database 112 to be hosted on a remote server). The computer 100 also includes input devices 140 (e.g., a keyboard, a mouse or other position-sensing device, etc.), by means of which a user can interact with the system, and a screen display 145. The computer 100 further includes a bidirectional system bus 150 over which the system components communicate.

The distribution of functionality shown in FIG. 1 is representative only and intended to provide one possible topology. It is possible to distribute the functionality illustrated in FIG. 1 among more or fewer computational entities as desired, and components may intercommunicate over a computer network, e.g., a wired or wireless local-area network (LAN), wide-area network (WAN) and/or other types of networks. When used in a LAN networking environment, components may be connected to the LAN through a network interface or adapter. When used in a WAN networking environment, components typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Some suitable communications protocols may include TCP/IP, UDP, or OSI, for example. For wireless communications, communications protocols may include the cellular telecommunications infrastructure, WiFi or other 802.11 protocol, Bluetooth, Zigbee, IrDa or other suitable protocol. Furthermore, components of the system may communicate through a combination of wired or wireless paths.

Figure 2:
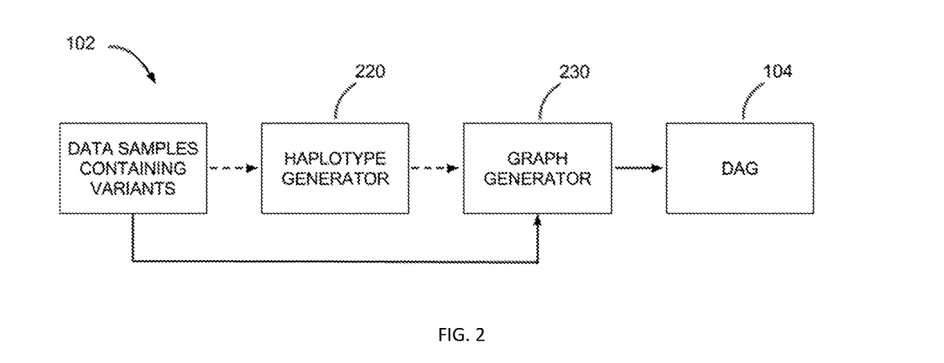
FIG. 2 is a block diagram of a representative graph generator in accordance with embodiments of the invention.

In operation, graph generator 102 creates a DAG encoding genomic variant data (e.g., allele frequency, variants, and optionally haplotypes). The functional modules of a representative graph generator 102 are illustrated in FIG. 2. Data samples containing genomic variants that distinguish the two copies of the relevant chromosome(s) (e.g., an SNP representing different nucleotides at the same position on the two chromosome copies, or "strands", which may be represented as a list of variants in a VCF file) may be obtained from, e.g., a sequencer 117 and information retrieval and analysis unit 115.

In some embodiments, a haplotype generator 220 further analyzes the data samples and detects haplotypes based on, e.g., the frequency at which certain variants occur together in the same subject. The generator 220 may be a conventional component, e.g., PLINK or HAPLOVIEW. (As noted, haplotypes are a set of SNPs located on one chromosome that are associated statistically, i.e., are observed in that particular combination in a significant number of individuals. Any software program that identifies these correlations could be used to insert haplotypes into the graph.) These components receive genotype (i.e., genomic sequence) data files in, e.g., VCF format for a population, specifying variant types and their chromosome positions, and generate allele and haplotype frequencies for that population. These frequencies represent the prevalence of particular alleles and haplotypes within the genome of the population.

The DAG generator 230 creates a DAG—i.e., a computational data structure in memory 125 representative of a DAG—encoding the frequency information. As shown in the embodiment of FIG. 2, the DAG can comprise variant frequency information, i.e., the frequency at which each variant is observed in the data samples. Additionally, the DAG can comprise haplotype information, reflecting the frequency at which certain combinations of variants are observed in the population. Haplotypes may be added to the DAG after the variants, e.g., by creating new nodes representing haplotypes and removing nodes containing variants present in haplotypes. Alternately, haplotypes may be added to the DAG prior to adding the variants. In either case, it is preferable that the DAG not contain multiple copies of the same variants (i.e. by including the same variant as both a variant node and within a haplotype node).

Figure 3A:
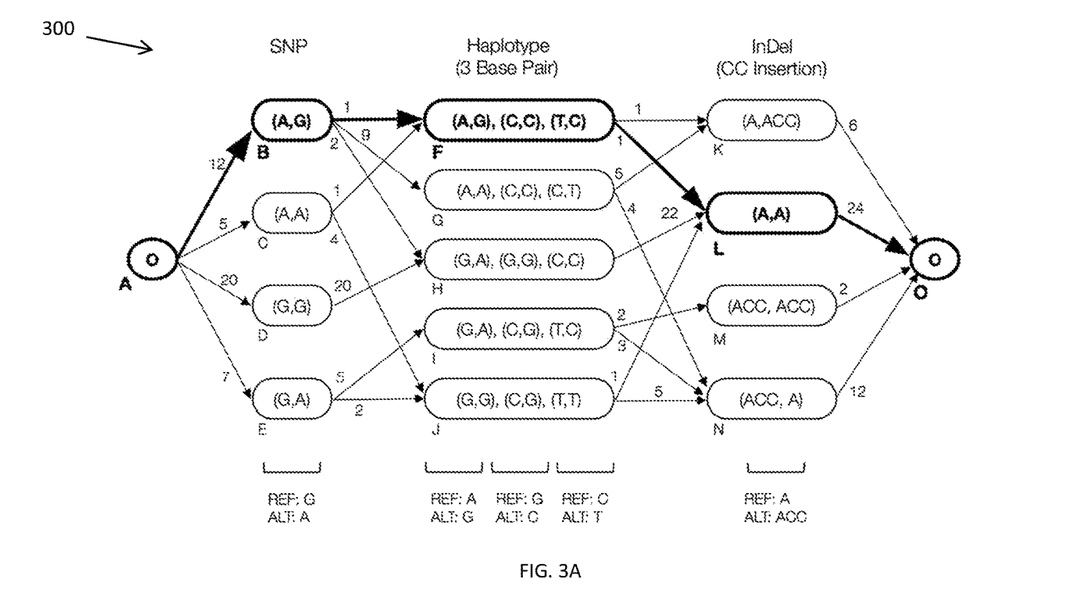
FIGS. 3A-3C graphically illustrate different representations of variant data.
Figure 3B:
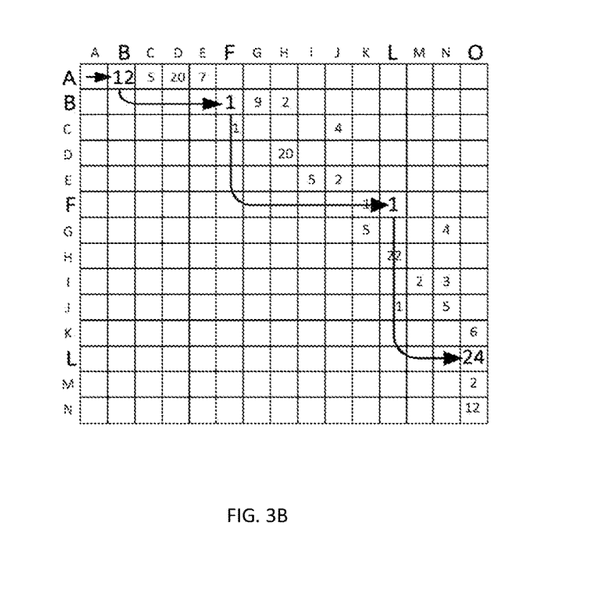

A representative DAG is illustrated conceptually in FIG. 3A. Each node of the DAG can contain variant information for both strands of a sample at a given physical location in order to preserve the zygosity information. The DAG defines edges as connections between genomic positions relative to a publicly available genomic reference. Edges maintain traversal information in the form of counts. Edge traversal counts are used to sample paths proportional to the observed path frequency. Thus, as shown in FIGS. 3A and 3B, the latter in the form of contingency table, the graph 300 has nodes corresponding to the same physical genome position and representing SNPs, haplotypes, and insertion/deletions. The leftmost edges connect the origin node to nodes representing SNP variant pairs. Node B, for example, represents the heterozygous SNP pair [A,G], meaning that one chromosome has A at the physical position corresponding to the node and the other has G; here G is the reference ("REF") and A is the alternate ("ALT") as indicated in the figure. B and E represent cases of heterozygous SNPs, whereas C and D represent cases of homozygous no SNP (i.e., REF), and homozygous SNP (i.e., ALT), respectively. The edges leading from A to B/C/D/E correspond to the frequency observed in the original sample data.

The next set of edges connect SNP nodes to haplotype nodes, each of which represents a sequence of SNPs that have been observed to occur together in the population. As can be seen, SNP nodes connect only to those haplotype nodes that are consistent with the SNP (and, of course, actually found in the population). Haplotype nodes F/G/H/I/J each comprise three nucleotides, with one possible alternate allele at each nucleotide site. At each of the three sites, it is possible to have a homozygous SNP (e.g., haplotype J, site 1), homozygous no SNP (e.g., haplotype G, site 1), or heterozygous SNP (e.g., haplotype F, site 1 and haplotype F, site 3).

Next in the sequence of variants is a set of nodes representing an InDel (here an insertion), which will either be "A" (reference allele) or a CC insertion to form "ACC" (alternate allele). Node K, for example, represents a heterozygous insertion in which one chromosome has the reference allele and one has the alternate allele. The highlighted traversal corresponds to the following, in which the first letter of each pair represents one chromosome and the second letter in each pair represents the second chromosome: (A,G), [(A,G), (C,C), (T,C)], (A, A). The traversal indicates a status (either REF or ALT) for five variants, in which three (in brackets) are in an observed haplotype.

Figure 3C:
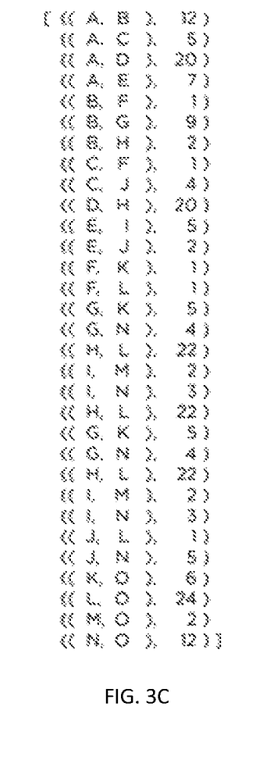

A specific path in the DAG from origin to terminus, e.g., the boldfaced path A→[A,G]→(A,G), [C,C], (T,C)→(A,A) O, can represent a particular individual in the analyzed population. Overlaying the paths for all members of the analyzed population facilitates frequency analysis. For convenience, each node may be labeled with a unique letter as shown. This facilitates representation of the graph in other forms, such as a contingency table as shown in FIG. 3B. The contingency table illustrates the frequency distribution of paths, with edge weights representing the frequency at which two nodes are connected in the analyzed population. In other words, the edge weights represent the frequency at which individuals in the population have variants that occur in that order. In FIG. 3C, the contingency table is represented as a set of tuples in order to reduce graph storage requirements.

It should be noted that the representative DAG shown in FIGS. 3A-C is only a representative example. In many applications, a DAG could comprise tens to hundreds of millions of nodes. For example, the 1000 Genomes Project performed whole-genome sequencing of a geographically diverse set of 2,504 individuals, yielding a broad spectrum of genetic variation including over 88 million known variants. Each or a subset of these variations could be included in a DAG according to the disclosure.

In various embodiments, the DAG is initialized as follows. A variant pair for each physical nucleic-acid position (corresponding to variants for each strand) is read in as a node, with attributes specifying a base pair (or base-pair sequence, in case of insertion or haplotype) present at that location. Each node includes a boolean value signifying the presence or absence of a variant in the reference genome.

Each edge between two variants is assigned a weight of 1, signifying that it has been traversed once in this sample. (Traversal is discussed below.) In some embodiments, DAG generator 230 assigns each node a hash value derived from the physical position and the variant's zygosity information (with two differently-phased heterozygous sites receiving two distinct hash values), i.e., whether the allele containing the node is homozygous or heterozygous in the two strands.

In one implementation, a separate VCF file is obtained for each individual. In each VCF file, a variant (the variant pair) is read and added to the graph. Haplotypes can be added at any point, but if the variants in the haplotype are already in the graph, they may be removed or condensed in some way. In another embodiment, nodes store only haploid information (i.e., just one haploid genotype for each pair). The second haploid genotype is added as a separate node. In this case, traversal of the graph would result in a haploid genome, so to get a full genome the graph is traversed twice. This approach is slower and less efficient storage-wise, however, so it is preferred to store the full zygosity in each node.

After the DAG is initialized, union operations may be performed to add samples to the graph. The union operator applies the node hash function to determine if sample variants are currently stored in the population graph. If the variant is not present, a node, along with edges leading to and from it, is added to the graph. Otherwise the weight of the edge between two nodes already present in the graph is increased by 1. Accordingly, the hash function facilitates rapid graph formation by increasing the speed with which node variants may be identified or determined to be absent. It also allows the graph to be assembled out of node order without increased computational burden.

The hash value is generated from the position and the particular bases in that node in order to guarantee uniqueness. The hashing function may be any suitable function, e.g., hash(x) in PYTHON according to the statement Name=float(hash(x) for x in zip(position, bases)). In this case the hash value is assigned to the (location, zygosity) tuple, where "position" is a number and "bases" is a tuple, for example, (A,G). Alternatively, "bases" may be a tuple (True, False), where True is Alt, and False is Ref; in the case of haplotypes, "bases" will be a list of tuples [(A,G), (C,G), (T, A)], rather than one tuple.

Indels may be appended to the reference allele as alternate alleles, and DAG generator 230 may implement the 1000 G notation for specifying insertions and deletions. The 1000 G convention represents insertions by including the reference allele preceding the insertion, as the reference, at a given position. The insertion is appended to the reference allele, as an alternative allele (for example REF=A, ALT=AGG for a GG insertion after an A in the reference). Similarly, the 1000 G convention defines deletions by providing a reference whose length spans multiple bases and a single-base alternative allele (for example ALT=TCCGA and REF=T for a CCGA deletion after T in the reference). The graph may maintain the 1000 G representation for simplicity of verifying structure and traversal, as well as to ensure that all variant paths are the same length.

Haplotypes are calculated using, e.g., PLINK and read into the graph as a single node per haplotype block. Haplotype information may be added to the graph by first calculating the haplotype blocks, and then reading in each set of contiguous SNPs present in those blocks as a single node. In one embodiment, haplotypes are defined as blocks of contiguous variant sets, where the proportion of variant pairs with strong linkage disequilibrium between variant pairs relative to those with strong evidence for historical recombination is greater than or equal to 19. The span of haplotype blocks may be limited to 200 kbp to simplify computation. The haplotype variant list may be traversed upon loading. Contiguous variants present in the haplotype set are unioned into tuples containing attributes present in SNP nodes. A hash value corresponding to a physical position within the initial variant's physical position and a tuple of tuples of variant sets becomes the node's value. A set of variants present in haplotype blocks may be maintained in order to coordinate between SNP and haplotype simulation.

Figure 4:
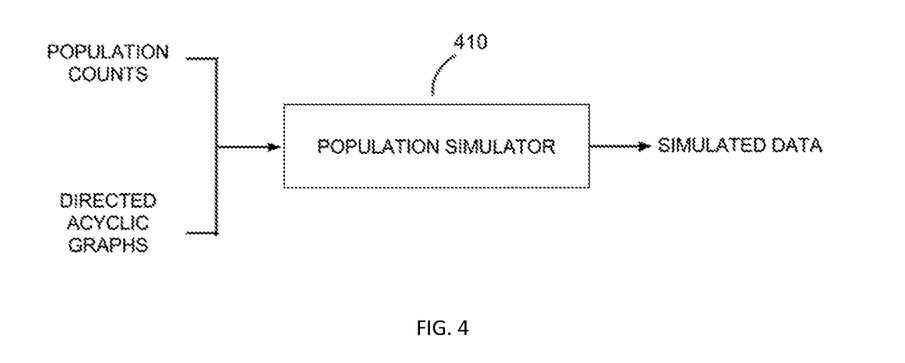
FIG. 4 is a block diagram of a representative population simulator in accordance with embodiments of the invention.

The population simulator 106 uses the DAG 104 to produce simulated genomic data based on one or more populations whose variant frequencies are encoded in one or more corresponding DAGs. In the representative embodiment shown in FIG. 4, the population simulator 106 includes a population simulator module 410 that receives population counts and a DAG 104 for each population to be analyzed and creates both multiple-population and individual simulations. The DAG may, for computational efficiency, be expressed as a contingency table or graph. To create multiple populations, simulator module 410 creates a set of graphs specific for those subpopulations (i.e., by creating each graph using only individuals from a particular subpopulation). To simulate individuals from different subpopulations, simulator module 410 thereupon generates a plurality of individuals using each particular graph. The number of individuals simulated is determined by the number of times the simulator 410 is run (i.e., the DAG is traversed).

Simulated data for a population is generated by probabilistic traversal of the corresponding DAG. Each individual graph, as well as the final graph, begin and end with terminal nodes as illustrated in FIG. 3A. Terminal nodes include a start node with a value equal to negative infinity, and a terminal node with a value equal to positive infinity. The edge weights in each individual DAG are all set to 1. In one embodiment, the individual graphs are successively merged to form the final graph, but in other embodiments, variants from the individual graphs are added to the final DAG on a node-by-node basis to reduce runtime and increase efficiency.

Graph traversal of the final graph can begin and end with terminal nodes, but also may begin or end at any particular nodes in the graph. For example, one may wish to simulate variants in a particular position of the genome. For computational efficiency, the graph may be represented as an adjacency list sorted by the value of the physical position corresponding to the start of each edge. During graph traversal, a weighted random function is called to choose a particular edge, where the probability of traversing an edge depends on how often two nodes connected by that edge were observed together in the sample set—i.e., the edge weight. This information may be converted into a contingency table as illustrated in FIGS. 3B and 3C, and sampling may be performed from this table. A set of traversed nodes is returned for each traversal, and these nodes collectively form a list of variants representing a simulated genome or genome subset over the traversed positions. The individual simulator 420 may convert a set of traversal lists (i.e., nodes) into a standard (e.g., VCF) file format, which allows for comparison graph traversals with available software tools.

For example, with reference to FIG. 3A, when choosing where to continue traversal from node B, there are three options—node F, G, and H. Edge (BF) has weight 1, edge (BG) has weight 9, and edge (BH) has weight 2. Since the sum of weights is 12, the probability of going down (BF) is 1/12, down (BG) is 9/12, and down (BH) is 2/12 (given that we are starting from node B). The random operation may choose one of the edges depending on those probabilities, or by making four intervals BF=[0, 1/12), BG=[1/12, 10/12), BH=[10/12, 12/12], and then calling a random function which returns a number k=[0,1], and choosing the edge into whose interval k falls.

As noted previously, each edge in the DAG provides an indication of the number of individuals in a population that had a sequence of two particular variants. This property increases the realism of simulated data, particularly when including haplotypes. Further, this property allows for both the fast construction and traversal of the graph, resulting in an extremely efficient method of genome simulation. However, for variants farther downstream of a given node, combinations not observed in the population may result. In most cases, this is useful as it allows for the simulation of many more unique genomes than were originally observed in the input data. In certain cases where this may not be desirable, one may wish to construct the DAG using only individuals for a smaller subregion or subpopulation, or perhaps including a larger number of haplotypes.

The foregoing methods provide a flexible approach for simulating population data, support subpopulation simulations, and provide scalable simulation tools and techniques. The simulation framework described above supports multiple sources of variant information, including SNP chip data specification with allele frequency information, subpopulation allele and haplotype information, and whole-genome variant data sources.

Any suitable programming language may be used to implement without undue experimentation the analytical functions described within. Illustratively, the programming language used may include assembly language, Ada, APL, Basic, C, C++, C*, COBOL, dBase, Forth, FORTRAN, Java, Modula-2, Pascal, Perl, Prolog, Python, REXX, and/or JavaScript, for example. Further, it is not necessary that a single type of instruction or programming language be utilized in conjunction with the operation of the system and method of the invention. Rather, any number of different programming languages may be utilized as is necessary or desirable.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of simulating genomic data using input data representing nucleic-acid sequences obtained by chemical analysis of biological samples obtained from a population of organisms, the population exhibiting a variant frequency, the method comprising the steps of:
   a. computationally representing the input data for the population exhibiting the variant frequency as a directed acyclic graph (DAG) data structure comprising a plurality of nodes and edges connecting the nodes, wherein the nodes include an origin node and a terminus node, each node corresponds to a genomic position and a variant type, and the edges have weights corresponding to the occurrences of nodes connected by edges in the input data; and
   b. repeatedly:
   computationally traversing a sequence of nodes of the DAG data structure starting from the origin node and terminating with the terminus node to create simulated genomic data for the population with maintaining variant frequency of the population for the input data, the traversed nodes corresponding to a first variant type representing a single-nucleotide polymorphism (SNP), a second variation type representing a haplotype and a third variation type representing insertion and deletion of a nucleotide, the traversal being performed probabilistically in accordance with the edge weights; and
   (ii) storing, in a database, the simulated genomic data corresponding to the traversal and converting the simulated genomic data into a standard file format; and
   (iii) updating the DAG data structure based on determination whether new variants or update counts of variants already present using a hash value assigned to each node by a hash function, the hash value being a unique value determined based on the genomic position and the variant type associated with each node.

2. The method of claim 1, wherein each node further stores zygosity information.

3. The method of claim 1, wherein the traversals are performed using a weighted random function.

4. The method of claim 1, further comprising repeating steps (a) and (b) for a plurality of populations.

5. The method of claim 4, further comprising the steps of:
   computationally representing input data from each of the populations as a separate DAG data structure; and
   wherein step (b) is performed on the separate DAG data structures to simulate individuals from each population.

6. The method of claim 1, wherein the computational representation step comprises:
   initializing the DAG data structure; and
   repeatedly adding entries to the DAG data structures or changing weights stored in the data structure and associated with existing entries by performing union operations on the DAG data structure and a new entry thereto.

7. The method of claim 6, wherein each node also comprises zygosity information and entries are added according to steps comprising:
   reading in a variant pair as a node;
   assigning a node hash value to the node, the node hash value being based at least in part on a genomic position and a zygosity of the variant pair associated with the node; and
   performing a union operation using the node hash value to determine if the variant pair associated with the node is already in the DAG data structure, and if not, increasing a weight of at least one edge of the DAG data structure that connects to the node.

8. The method of claim 1 wherein the DAG is created using a set of genotypes for each individual organism in the population.

9. The method of claim 1, wherein the simulated genomic data is a simulated genome, a simulated genome subset, a simulated chromosome, or a list of simulated genomic variants.

10. The method of claim 1, wherein the DAG data structure does not store variants that are homozygous for reference sequence.

11. The method of claim 1, wherein computationally representing the input data as a DAG data structure further comprises calculating haplotypes from the input data, wherein each haplotype is computationally stored in the DAG data structure as a node.

12. The method of claim 11, wherein the haplotype comprises a set of variants that are statistically correlated with one another.

13. A system for simulating genomic data using input data representing nucleic-acid sequences obtained by chemical analysis of biological samples obtained from a population of organisms, the population exhibiting a variant frequency, the system comprising:
- a computer memory;
- a graph generator for computationally representing the input data for the population exhibiting the variant frequency as a data structure in the memory encoding a directed acyclic graph (DAG) comprising a plurality of nodes and edges connecting the nodes, wherein the nodes include an origin node and a terminus node, each node specifies a genomic position and a variant type, and the edges have associated weights corresponding to the occurrences of nodes connected by edges in the input data; and
- a population simulator for simulating variant datasets by repeatedly:
  (i) traversing a sequence of nodes of the DAG data structure starting from the origin node and terminating with the terminus node to create simulated genomic data for the population with maintaining variant frequency of the population for the input data, the traversed nodes corresponding to a first variant type representing a single-nucleotide polymorphism (SNP), a second variation type representing a haplotype and a third variation type representing insertion and deletion of a nucleotide, the traversal being performed probabilistically in accordance with the edge weights; and
  (ii) storing, in the computer memory, the simulated genomic data corresponding to the traversal and converting the simulated genomic data into a standard file format,
- the graph generator is further configured to update the DAG data structure based on determination whether new variants or update counts of variants already present using a hash value assigned to each node by a hash function, the hash value being a unique value determined based on the genomic position and the variant type associated with each node.

14. The system of claim 13, wherein each node further comprises zygosity information.

15. The system of claim 13, wherein the population simulator is configured to traverse the sequence of nodes using a weighted random function.

16. The system of claim 15, wherein the population simulator is configured to repeat (i) and (ii) for a plurality of populations.

17. The system of claim 16, wherein the graph generator is configured to computationally represent input data from each of the populations as a separate DAG, and the population simulator is configured to simulate individuals from each separate DAG.

18. The system of claim 13, wherein the graph generator is configured to initialize the DAG and repeatedly add entries thereto or change weights associated in the data structure with existing entries by performing union operations on the DAG and a new entry.

19. The system of claim 18, wherein each node also comprises zygosity information and the graph generator is configured to add entries by:
- temporarily storing, in the data structure, a variant pair as a node;
- assigning a node hash value to the node, the node hash value being based at least in part on a genomic position and a zygosity of the variant pair associated with the node; and
- performing a union operation using the node hash value to determine if the variant pair associated with the node is already in the DAG data structure, and if not, increasing a weight of at least one edge of the DAG data structure that connects to the node.

20. The system of claim 13, wherein the simulated genomic data is a simulated genome, a simulated genome subset, a simulated chromosome, or a list of simulated genomic variants.

21. The system of claim 13, wherein the graph generator is further configured to not include homozygous reference variants in the DAG data structure.

* * * * *